(12) United States Patent
Madabhushi et al.

(10) Patent No.: US 9,851,421 B2
(45) Date of Patent: Dec. 26, 2017

(54) DIFFERENTIAL ATLAS FOR CANCER ASSESSMENT

(71) Applicant: Case Western Reserve University, Cleveland, OH (US)

(72) Inventors: Anant Madabhushi, Beachwood, OH (US); Mirabela Rusu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 89 days.

(21) Appl. No.: 14/960,539

(22) Filed: Dec. 7, 2015

(65) Prior Publication Data

US 2016/0196647 A1 Jul. 7, 2016

Related U.S. Application Data

(60) Provisional application No. 62/099,665, filed on Jan. 5, 2015.

(51) Int. Cl.
*G06K 9/00* (2006.01)
*G01R 33/34* (2006.01)
(Continued)

(52) U.S. Cl.
CPC ...... *G01R 33/34084* (2013.01); *A61B 5/4381* (2013.01); *G06K 9/6255* (2013.01); *G06K 9/6284* (2013.01); *G06T 7/0014* (2013.01); *G06T 7/337* (2017.01); *G06T 19/20* (2013.01); *G01R 33/5608* (2013.01);
(Continued)

(58) Field of Classification Search
CPC .......... G01R 33/34084; G01R 33/5608; G06K 9/6255; G06K 9/6284; G06T 7/337; G06T 7/0014; G06T 19/20; G06T 2210/41; G06T 2219/2016; G06T 2207/30081; G06T 2207/10088; A61B 5/4381
See application file for complete search history.

(56) References Cited

U.S. PATENT DOCUMENTS 9,025,841 B2 * 5/2015 Wels .................... G06K 9/6207
382/131
2006/0245629 A1 * 11/2006 Huo ...................... G06T 7/0012
382/131
(Continued)

*Primary Examiner* — John Strege
(74) *Attorney, Agent, or Firm* — Eschweiler & Potashnik, LLC

(57) ABSTRACT

Methods and apparatus associated with producing a quantification of differences associated with biochemical recurrence (BcR) in a region of tissue demonstrating prostate cancer (PCa) are described. One example apparatus includes a set of logics, and a data store that stores a set of magnetic resonance (MR) images acquired from a population of subjects. The set of logics includes an image acquisition logic that acquires a diagnostic image of a region of tissue in a patient demonstrating PCa, a morphology logic that extracts a shape feature, a volume feature, or an intensity feature from the diagnostic image or from a member of the set of MR images, a differential atlas construction logic that constructs a statistical shape differential atlas from the set of MR images, and a quantification logic that produces a quantification of differences based on the shape feature, the volume feature, or the intensity feature, and the differential atlas.

21 Claims, 7 Drawing Sheets

(51) Int. Cl.
*A61B 5/00* (2006.01)
*G06T 7/00* (2017.01)
*G06T 19/20* (2011.01)
*G06T 7/33* (2017.01)
*G06K 9/62* (2006.01)
*G01R 33/56* (2006.01)

(52) U.S. Cl.
CPC ............... *G06T 2207/10088* (2013.01); *G06T 2207/30081* (2013.01); *G06T 2210/41* (2013.01); *G06T 2219/2016* (2013.01)

(56) References Cited

U.S. PATENT DOCUMENTS

| | | | |
|---|---|---|---|
| 2007/0019846 A1* | 1/2007 | Bullitt | G06T 7/0014 382/128 |
| 2010/0266185 A1* | 10/2010 | Matulewicz | G06K 9/62 382/131 |
| 2010/0329529 A1* | 12/2010 | Feldman | G06K 9/6252 382/131 |
| 2011/0243417 A1* | 10/2011 | Madabhushi | G06K 9/3233 382/131 |
| 2011/0299750 A1* | 12/2011 | Cool | G06T 17/10 382/131 |
| 2012/0155734 A1* | 6/2012 | Barratt | G06T 7/35 382/131 |
| 2012/0163693 A1* | 6/2012 | Suri | G06T 7/0012 382/131 |
| 2013/0080134 A1* | 3/2013 | Donovan | G06F 19/3437 703/11 |
| 2014/0029823 A1* | 1/2014 | Birkbeck | G06T 7/0081 382/131 |
| 2014/0294272 A1* | 10/2014 | Madabhushi | G06T 7/0014 382/131 |
| 2015/0245817 A1* | 9/2015 | Stone | A61B 90/39 600/443 |
| 2015/0371384 A1* | 12/2015 | Wong | G06T 7/0016 382/103 |
| 2016/0171695 A1* | 6/2016 | Jacobs | A61B 5/055 382/131 |
| 2016/0266126 A1* | 9/2016 | Shipitsin | C12Q 1/6886 |
| 2016/0364880 A1* | 12/2016 | Barratt | G06T 7/0089 |
| 2017/0084021 A1* | 3/2017 | Athelogou | G06T 7/0012 |
| 2017/0169276 A1* | 6/2017 | Agaian | G06K 9/0014 |

* cited by examiner

DIFFERENTIAL ATLAS FOR CANCER ASSESSMENT

CROSS REFERENCE TO RELATED APPLICATIONS

This application claims the benefit of U.S. Provisional Application 62/099,665 filed Jan. 5, 2015.

BACKGROUND

Magnetic resonance (MR) imaging is routinely used to diagnose prostate cancer (PCa) and identify the stage of PCa. PCa may induce changes in the shape of the prostate capsule and central gland (CG) in biopsy positive (Bx+) patients relative to biopsy negative (Bx−) patients, elevated-prostate specific antigen (PSA) patients, or normal patients. PCa may also induce changes in the volume of the prostate and CG in Bx+ patients relative to Bx−, elevated-PSA, and normal patients. These changes in the shape and volume of the prostate may be observed in T2 weighted (T2w) MRI images.

Radiation therapy is a common treatment for PCa. However, radiation therapy has been reported to have failure rates as high as 25%. Predicting biochemical recurrence (BcR) prior to radiation therapy may enable better planning and personalization of treatment. MR images may be used to assist the prediction of BcR in PCa patients. However, when obvious extra-capsular spread of the disease is not present, conventional approaches employing MRI are not useful for distinguishing patients who will experience BcR from those who will not.

Multi-parametric MRI is widely used in the management of PCa to improve the localization and local staging of the disease. Despite its broad adoption in the management of PCa, conventional approaches using MRI may suffer from a large variability in MRI acquisition parameters and reporting. This large variability may occur both within an individual institution (e.g., hospital, university) and across multiple institutions. Conventional approaches to MRI-based PCa diagnosis and identification may employ protocols or guidelines for imaging acquisition parameters and findings reporting, although score interpretation and detection thresholds, particularly across multiple institutions, have not been uniformly applied or exhaustively studied. Furthermore, implementing protocols and guidelines across different institutions takes time, costs money, and puts a patient at additional risk if the guidelines and protocols are not consistently applied.

One conventional approach to reduce the subjectivity of image appearance assessment and score assessment includes employing computer aided detection and diagnosis (CADx) techniques. Conventional CADx approaches typically employ image-driven textures acquired from multiple MRI protocols, and may combine the image-driven textures with pharmacokinetic behavior quantifiers and machine learning techniques. However, these conventional approaches have not been generalized across different scanners or across different institutions.

Conventional MRI protocols may also lack tissue-specific numerical meaning. A lack of tissue-specific numerical meaning may result in inconsistent MRI intensities, even for the same patient, the same scanned region, or the same scanner. The impact of inconsistent MRI intensities within the same patient, same scanned region, or same scanner may be exacerbated across multiple institutions. Thus, conventional approaches to PCa diagnosis and management using MRI are less than optimally accurate or efficient, and may not optimally utilize information gathered across different populations by different institutions.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Variations in prostate shape and volume may be related to patient prognosis and outcome. Prostate structures may show differences in volume and shape when comparing at risk Bx+ populations with Bx− populations. The prostate may demonstrate shape differences at the prostate apex when comparing Bx+ populations with normal populations. Example apparatus and methods rely on data acquired using a systematic investigation of the differences in the shape of the prostate capsule or CG on T2w MRI between patients with and without prostate cancer, or between patients exhibiting BcR and patients not exhibiting BcR. The data is combined into a statistical shape atlas. A statistical shape atlas is a subgroup of population studies. Statistical shape atlases combine information from multiple subjects into one unified representation. Example methods and apparatus generate a quantification of differences between different statistical shape atlases, or between an image of a patient demonstrating PCa pathology and a statistical shape atlas. Example methods and apparatus may generate the quantification of differences by identifying and characterizing differences in the shape of the prostate capsule or CG. Example apparatus and methods use differences in the shape of the prostate capsule or CG to distinguish a patient with normal prostate from a patient with a cancerous prostate. Example methods and apparatus thus facilitate predicting BcR in patients demonstrating PCa.

Figure 7:
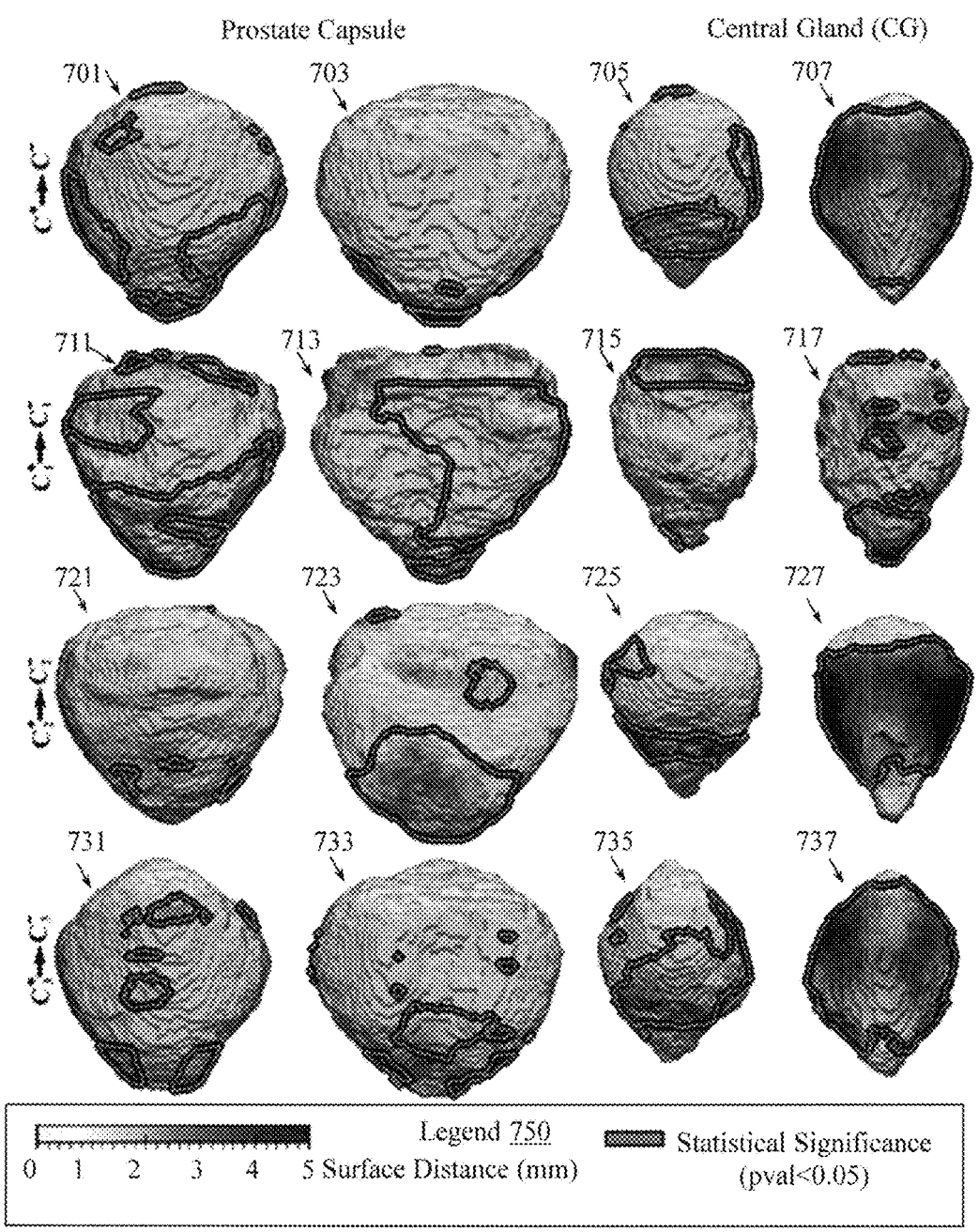
FIG. 7 illustrates statistically significant surface distance differences between subpopulations of subjects.

In one implementation, shape differences between the capsule and CG or T2w MR images between 36 PCa− and 156 PCa+ subjects were investigated using a statistical shape atlas. A confirmation of the presence or absence of cancer was based on a needle biopsy. The normal and PCa+ populations were imaged using techniques including 1.5 Tesla (T) and 3 T T2w MR imaging. Two separate atlases were constructed by mapping images acquired from the PCa− and PCa+ populations in a single canonical representation. Wilcoxon sum rank tests and multiple comparison Bonferroni corrections were subsequently applied to identify significant shape differences on the prostate capsule and the CG between the PCa− and PCa+ atlases. Statistically significant differences were identified for the prostate capsule and CG shape between the PCa− and PCa+ patients. A summary of these differences is illustrated in FIG. 7. In one implementation, differences in distances as large as 31 mm and 1.1 mm were identified on the anterior apex of the capsule and at the border of the CG and peripheral zone.

Anterior prostate cancers are difficult to biopsy. This difficulty may result in delays in identification of the disease which may in turn cause more substantial deformations in the capsule shape for the anterior tumors. Example methods and apparatus, by accessing and utilizing collections of MR images acquired across multiple institutions, improve on conventional approaches to detecting and predicting BcR when the cancer affects the anterior prostate. Example methods and apparatus may also identify shape differences on T2w MR images in the anterior apex of the prostate and at the border of anatomic sub-regions between PCa+ and PCa− patients. Example methods and apparatus may employ automated computerized analysis of prostate shape on T2w MR images to complement radiographic features of disease appearance (e.g., intensity, textures) in diagnostic decision making. Since a more accurate BcR prediction is made, example apparatus and methods thus predict patient outcomes in a more consistent and reproducible manner than conventional approaches.

By generating statistical shape atlases from medical imagery acquired from different institutions using different acquisition parameters, example methods and apparatus produce the concrete, real-world technical effect of utilizing disparate collections of imagery that would otherwise be unrelated and underutilized, while increasing the accuracy of the evaluation. Additionally, example apparatus and methods increase the probability that at-risk patients receive timely treatment tailored to the particular pathology they exhibit. Example methods and apparatus may also reduce the number of invasive procedures needed to accurately predict BcR in Pa patients. The additional technical effect of reducing the expenditure of resources and time on patients who are less likely to suffer BcR or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
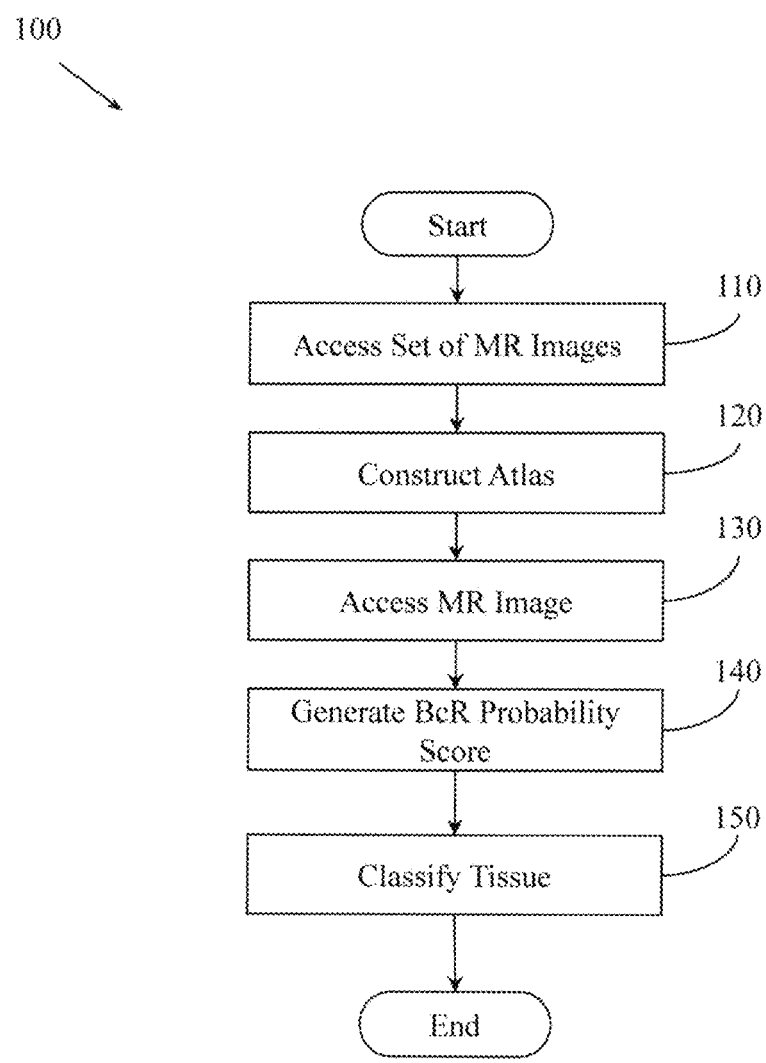
FIG. 1 illustrates an example method of predicting BcR in a region of tissue demonstrating PCa pathology.

FIG. 1 illustrates an example computerized method 100 for predicting BcR. In one embodiment, method 100 includes identifying and characterizing differences induced by BcR in a region of tissue demonstrating PCa pathology. Method 100 includes, at 110, accessing a set of MR images acquired from a population of patients. A member of the set of MR images includes a prostate capsule shape attribute, a prostate capsule volume attribute, a CG shape attribute, or a CG volume attribute. The CG includes a prostate central zone (CZ) and a prostate transitional zone (TZ). The border of the TZ and the CZ is difficult to assess in 3D T2w MR imagery. Example methods and apparatus improve on conventional approaches by combining the TZ and CZ into the CG, increasing the speed and accuracy with which the CG may be studied. The population includes a set of subpopulations. In one embodiment, the set of subpopulations includes a PCa+ subpopulation, a PCa− subpopulation, or a normal subpopulation. A PCa− subpopulation may be a subpopulation in which members of the subpopulation demonstrate increased prostate specific antigen (PSA). A PCa+ subpopulation may be confirmed by needle biopsy (Bx+). A PCa− population may also be confirmed by needle biopsy (Bx−). In another embodiment, MR images of other, different subpopulations may be accessed.

Prostate shape and volume varies naturally. Prostate shape and volume may also be influenced by benign conditions, including benign prostatic hyperplasia. Example methods and apparatus assess intra-class variability and compare intra-class variations with inter-class differences. For example, example methods and apparatus may assess shape, volume, or intensity variability within a PCa+ subpopulation, and also compare differences between the PCa+ subpopulation and a PCa− subpopulation.

In one embodiment of method 100, subpopulations may be acquired across a plurality of institutions. For example, a first subpopulation may be acquired by a first institution, while a second subpopulation may be acquired by a second, different institution. In one example, the first institution may be a university that acquires a set of MR images from patients identified as PCa+, while the second institution may be a hospital that acquires a set of MR images from patients identified as PCa−. In other embodiments, MR images may be acquired from other types or numbers of institutions.

Members of the set of MR images may be acquired using different acquisition parameters. In one embodiment of method 100, a first member of the set of MR images is acquired using a first set of MR acquisition parameters having a first set of values, and a second member of the set of MR images is acquired using a second, different set of MR acquisition parameters having a second, different set of values. The first set of MR acquisition parameters and the second set of MR acquisition parameters include image dimensions measured in pixels, resolution, or slice spacing. In one embodiment, a member of the set of MR images may be acquired with dimensions of 192 by 1024 pixels, 240 by 1024 pixels, 192 by 320 pixels, 240 by 320 pixels, 512 by 512 pixels, or 1024 by 1024 pixels. In one embodiment, a member of the set of MR images may be acquired with a resolution or 0.21-0.97 mm, 0.21-0.9 mm, 0.37-0.97 mm, 0.50-0.90 mm, 0.35 mm, or 0.21 mm. In one embodiment, a member of the set of MR images may be acquired with a slice spacing of 1.5-3.5 mm, 3.0-3.4 mm, 1.5-3.0 mm, 3.0-4.0 mm, or 3.0-3.5 mm. In other embodiments, other acquisition parameters and values may be employed.

Accessing the set of MR images may include accessing an MR image of a region of prostate tissue. The MR image may be stored, for example, in a computer memory or may be provided across a computer network. In one embodiment, the MR image is a 1.5 Tesla T2w MR image or a 3T T2w MR image. In another embodiment, other images sizes or other imaging techniques may be employed.

Method 100 also includes, at 120, constructing a statistical shape atlas from the set of MR images. The statistical shape atlas brings T2w MR images into a common frame of reference while ensuring the deformable alignment of the prostate capsule and CG within a population. The statistical shape atlas thus accounts for variations in intensity and shape within anatomic regions across different populations. In one embodiment, a first member of the set of MR images associated with a subpopulation is elastically aligned relative to a second member of the set of MR images associated with the subpopulation. The first member and the second member may be elastically aligned or registered using anatomically constrained registration that facilitates keeping the prostate capsule and CG aligned during atlas construction. Other registration approaches may be employed.

Method 100 also includes, at 130, accessing an MR image of a region of prostate tissue in a patient demonstrating cancerous pathology. The MR image of the region of prostate tissue has a prostate capsule shape attribute, a prostate capsule volume attribute, a CG shape attribute, or a CG volume attribute. The MR image may be a 1.5 Tesla T2w MR image or a 3 T T2w MR image. In one embodiment, the member of the set of MR images or the MR image is acquired using a surface coil or using an endorectal coil. In another embodiment, other images sizes or other imaging techniques may be employed.

Method 100 also includes, at 140, producing a quantification of differences between the MR image of the region of prostate and the statistical shape atlas. The quantification of differences may represent the difference in shape, volume, intensity, or texture between a region of prostate in a patient and a statistical shape atlas. The quantification of differences may be based, at least in part, on a comparison of the prostate represented in the MR image of the region of prostate tissue in the patient demonstrating cancerous pathology with the statistical shape atlas. The comparison may be based, at least in part, on attributes associated with the prostate represented in the MR image. The attributes of the prostate represented in the MR image compared with the statistical shape atlas may include the prostate capsule shape attribute, the prostate capsule volume attribute, the CG shape attribute, or the CG volume attribute of the MR image of the region of prostate tissue demonstrating cancerous pathology. The comparison may also be based on an MR intensity captured by the MR image. In one embodiment, method 100 generates a characterization of the MR image of the region of prostate tissue by identifying and characterizing differences induced by BcR in the MR image of the region of prostate tissue in the patient demonstrating cancerous pathology. The characterization may be based on the comparison.

Method 100 also includes, at 145, generating a BcR probability score associated with the MR image of the region of prostate tissue in the patient demonstrating cancerous pathology. The BcR probability score may represent the probability that the patient associated with the MR image will develop BcR within a period of time. The BcR probability score may be based on the quantification of differences.

Method 100 also includes, at 150, classifying the MR image of the region of prostate tissue in the patient demonstrating cancerous pathology. Classifying the MR image may include controlling a CADx system to generate a classification of the region of tissue in the image based, at least in part, on the quantification of differences or on the BcR probability score. The classification may indicate a likelihood that the patient will experience BcR within a time period. The time period may be one year, five years, or another time period.

In one embodiment, method 100 further includes annotating the prostate capsule or the CG represented in a member of the set of MR images or in the MR image of the region of prostate tissue demonstrating cancerous pathology. Annotating the prostate capsule or the CG may include automatically annotating the prostate capsule or the CG. In one embodiment, T2w MR images of the prostate capsule or the CG may be annotated using MeVisLab software. In another embodiment, an expert pathologist may annotate the prostate capsule or the CG.

Example methods and apparatus facilitate applying a more appropriately determined treatment based on the quantification of differences or the BcR probability. Using a more appropriately determined and applied treatment may lead to less therapeutics being required for a patient or may lead to avoiding or delaying a biopsy, a resection, or other invasive procedure. When regions of cancerous tissue, including the prostate capsule and CG detected in MR images, are more quickly and more accurately classified as likely or unlikely to experience BcR, patients with poorer prognoses may receive a higher proportion of scarce resources (e.g., therapeutics, physician time and attention, hospital beds) while those with better prognoses may be spared unnecessary treatment, which in turn spares unnecessary expenditures and resource consumption. Example methods and apparatus may thus have the real-world, quantifiable effects of improving patient outcomes and reducing resource expenditure.

While FIG. 1 illustrates various actions occurring in serial, it is to be appreciated that various actions illustrated in FIG. 1 could occur substantially in parallel. By way of illustration, a first process could access a set of MR images from a population of patients, a second process could construct a statistical shape atlas, and a third process could generate quantification of differences. While three processes are described, it is to be appreciated that a greater or lesser number of processes could be employed and that lightweight processes, regular processes, threads, and other approaches could be employed.

Figure 2:
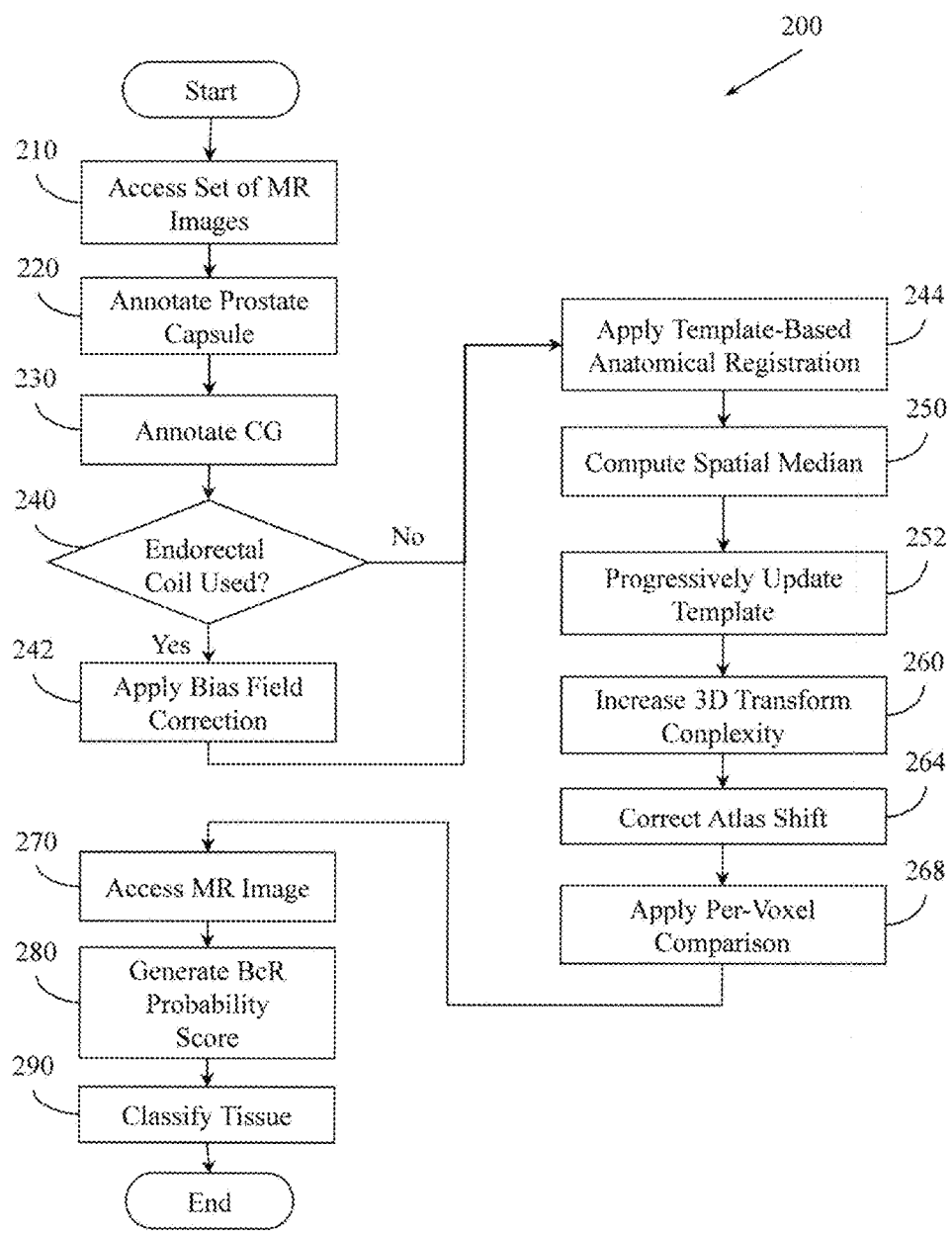
FIG. 2 illustrates an example method of predicting BcR in a region of tissue demonstrating PCa pathology.

FIG. 2 illustrates an example method 200 for predicting BcR in a region of tissue demonstrating PCa pathology. Method 200 is similar to method 100 but includes additional actions 220-268 associated with constructing a statistical shape atlas. Method 200 includes, at 210, accessing a set of MR images acquired from a population of patients, similar to action 110 described above.

Method 200 also includes, at 220, annotating a prostate capsule represented in a member of the set of MR images. Method 200 also includes, at 230, annotating a CG represented in the member of the set of MR images. The prostate capsule or the CG may be annotated by an expert pathologist, or the prostate capsule or the CG may be annotated automatically. In one embodiment, annotating the prostate capsule or the CG is performed using MeVisLab software.

Method 200 also includes, at 240, determining if the member of the set of MR images was acquired using an endorectal coil Images acquired with endorectal coils may exhibit artifacts manifested as hyper-intense signal around the endorectal coil. Conventional approaches may not account for these artifacts. If method 200 determines that the member of the set of MR images was acquired using an endorectal coil, method 200, at 242, applies bias field correction for the member of the set of MR images that was acquired using an endorectal coil.

Method 200 includes, at 244, applying template-based anatomically constrained registration to a subset of the set of MR images associated with a subpopulation. In one embodiment, anatomically constrained registration is based, at least in part, on a prostate capsule shape attribute, a prostate capsule volume attribute, a CG shape attribute, or a CG volume attribute. The anatomically constrained registration may also be based on a T2w intensity associated with the member of the set of MR images. Anatomically constrained registration ensures that subjects within a subpopulation are mapped into a common frame of reference, by explicitly considering the T2w MRI intensity as well as the annotated outlines of the prostate capsule or CG when optimizing the spatial alignment. Anatomically constrained registration ensures that both prostate and CG are in alignment relative to the registration references, and also to the other subjects in the subpopulation. The registration template captures the subpopulation anatomic characteristics, such as the shape and volume of the prostate and CG.

Method 200 also includes, at 250, computing a spatial median of shape attributes or volume attributes. The spatial median may be computed for the prostate capsule shape attribute or the CG shape attribute for the subset of the set of MR images associated with a subpopulation. The spatial median may also be calculated for the prostate capsule volume attribute or the CG volume attribute for the subset. In another embodiment, other statistical measures of the shape attribute or volume attribute may be computed.

Method 200 also includes, at 252, progressively updating the template used at step 244 for the template-based anatomical registration. Updating the template may be based, at least in part, on the spatial median of the prostate capsule shape attribute or the spatial median of the CG shape attribute. Updating the template may also be based, at least in part, on the spatial median of the prostate capsule volume attribute, or the spatial median of the CG volume attribute. In another embodiment, the template may be progressively updated based on other properties of a member of the set of MR images.

Method 200 also includes, at 260, progressively increasing the complexity of an optimized three dimensional (3D) transformation. The 3D transformation may be used to register a member of the set of MR images to another, different member of the set of MR images. The 3D transformation may be a translation. In one embodiment, progressively increasing the complexity of the optimized 3D transformation includes converting the 3D transformation from a first type of transformation to a second, different transformation. For example, the optimized 3D transformation may be converted from a translation to an affine translation. In one embodiment, upon computing the affine translation, method 200 may compute an elastic deformation. In another embodiment, the optimized 3D transformation may be converted to other types of transformations, using other, different approaches.

In one embodiment, method 200 determines whether a threshold complexity of the optimized 3D transformation has been achieved. Upon determining that the threshold complexity of the optimized 3D transformation has not been achieved, method 200 may repeat actions 244, 250, and 252. Upon determining that the threshold complexity of the optimized 3D transformation has been achieved, method 200 proceeds to action 264.

Method 200 also includes, at 264, correcting an atlas shift between an atlas associated with a first subpopulation and an atlas associated with a second subpopulation. In one embodiment, correcting the atlas shift between the atlas associated with the first subpopulation and the atlas associated with the second subpopulation includes optimizing the affine translation relative to the first subpopulation and the second subpopulation. In one example, the affine translation optimization is based, at least in part, on the prostate capsule shape attribute or the CG shape attribute. In another embodiment, the affine translation may be optimized using other techniques.

Method 200 also includes, at 268, comparing members of a first subset of the set of MR images with members of a second subset of MR Images. In one embodiment, comparing members of different subsets includes applying a per-voxel comparison between members of a subset of MR images associated with the first subpopulation and members of a subset of MR images associated with the second, different subpopulation. In one embodiment, the per-voxel comparison includes a non-parametric Wilcoxon test. In another embodiment, the per-voxel comparison further includes applying multiple comparison correction using a Bonferonni correction. In another embodiment, comparing members of different subsets may include other, different tests or corrections.

Method 200 also includes, at 270, accessing an MR image of a region of prostate tissue demonstrating PCa. The MR image includes a prostate capsule shape attribute, a prostate capsule volume attribute, a CG shape attribute, or a CG volume attribute. Method 200 also includes, at 280, generating a quantification of differences based, at least in part, a comparison of the MR image of the region of prostate tissue demonstrating PCa with the statistical shape atlas. Method 200 also includes, at 285, generating a BcR probability score based, at least in part, on the quantification of differences. Method 200 also includes, at 290, classifying the region of tissue based, at least in part, on the quantification of differences or the BcR probability score.

Figure 6:
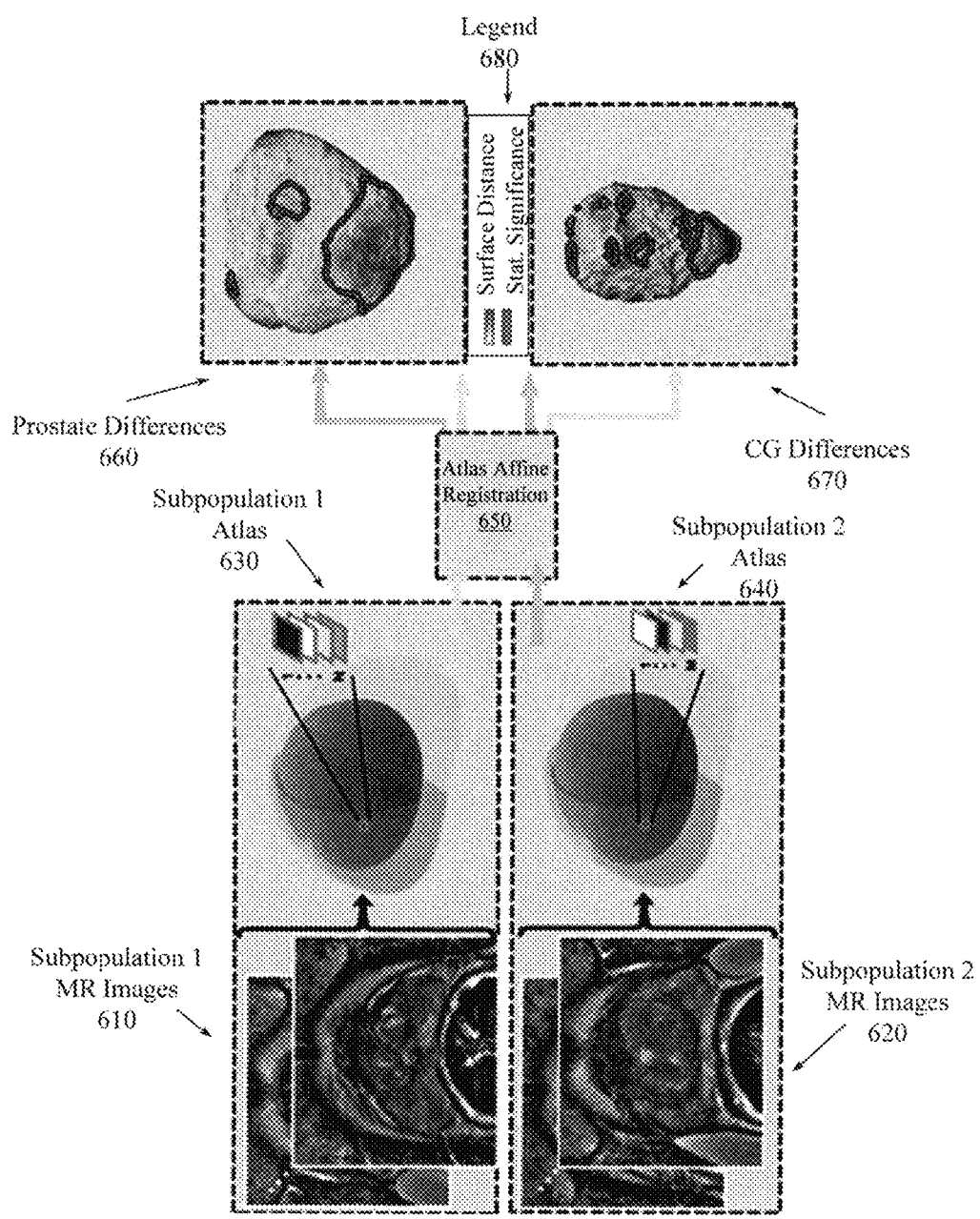
FIG. 6 illustrates a data flow associated with an example implementation of methods and apparatus described herein.

FIG. 6 illustrates a data flow associated with an example implementation of differential atlas construction and statistical comparison that may be employed by methods and apparatus described herein. FIG. 6 summarizes one possible implementation for the construction of a differential shape atlas used for comparing images acquired from subpopulations of subjects demonstrating PCa+, PCa−, or normal pathologies. Conventional approaches for quantifying differences between different populations of prostates, or for predicting BcR, may perform per-voxel comparisons, but conventional approaches do not effectively handle the large variety of prostate or CG volumes across different subpopulations. Example methods and apparatus may map a subpopulation or subpopulations into a common frame of reference using anatomically constrained registration. For example, a set of one through N, where N is an integer, subpopulation 1 MR images 610 may be registered using anatomically constrained registration. Another set of one through M, where M is an integer, subpopulation 2 MR images 620 may also be registered using anatomically constrained registration. Since, in this example, the construction of the subpopulation 1 atlas 630 is performed independently of the construction of the subpopulation 2 atlas 640, translation or rotation shifts relative to the different atlases may occur.

Example methods and apparatus correct atlas shift. In the example illustrated in FIG. 6, atlas shift is corrected by optimizing an atlas affine transformation of the first atlas 630 relative to the second atlas 640. In this example, the alignment of the atlas affine registration 650 is driven by the prostate shape. In another example, the alignment of the atlas affine registration 650 may be driven by the CG shape, or by other features. Example methods and apparatus apply statistical tests to compare the shape or volume features of the prostate capsules or CGs described in the differential shape atlases. In the example illustrated in FIG. 6, a per-voxel non-parametric Wilcoxon test is employed to evaluate the statistical significance of morphological shape differences. Multiple comparison correction may be performed by example methods and apparatus using a Bonferonni correction, or other correction techniques. In the example illustrated in FIG. 6, the multiple comparison correction includes dividing surface voxels' p-values by the number of comparisons performed. In this example, the number of comparisons performed is equal to the number of surface voxels of either the prostate capsule or the CG. In one embodiment, statistical comparison may be addressed after multiple comparison corrections results in a p-value of p<0.05. Prostate differences 660 illustrates regions of statistically significant surface differences associated with the prostate capsule shape between the different subpopulations. CG differences 670 illustrates statistically significant surface differences associated with the CG shape between the different subpopulations. Legend 680 indicates the outline and visual cues used to indicate regions of statistically significant surface distance differences represented by prostate differences 660 and CG differences 670.

FIG. 7 illustrates figures with statistically significant surface distance differences between subpopulations. FIG. 7 thus illustrates one possible example of a graphical representation of a quantification of differences. FIG. 7 illustrates surface representations of prostate capsules or CGs that may be associated with PCa pathology. FIG. 7, elements 701, 711, 721, and 731 (column 1), and 703, 713, 723, and 733 (column 2) illustrate surface representations that show shape differences between atlases on the prostate capsule. FIG. 7, elements 705, 715, 725, and 735 (column 3) and 707, 717, 727, and 737 (column 4) illustrate surface representations that show shape differences between atlases on the CG. Columns 1 and 3 show the anterior side of the prostate capsule or the CG, while columns 2 and 4 show the posterior side of the prostate capsule or CG, near the rectal wall. Shades of grey indicate spatial distances between the two atlases on a scale of 0 mm to 5 mm, while the darker outline indicated in legend 750 is used to show the regions of statistical significance of the difference, where the difference is computed based on the mapped subjects.

PCa+ and PCa− subjects may demonstrate morphological differences on the left and right side of the prostate, while statistically significant differences may be apparent on CGs on the posterior side. The CG shape differences are the outcome of CG overall volume differences, based on CG hypertrophy in the Bx− subjects. Example methods and apparatus effectively capture these morphological differences and apply them when generating a quantification of differences or calculating a BcR probability score.

FIG. 7 further illustrates a comparison of PCa+ and PCa− subjects from different institutions in elements 711-737. The comparison of $C_1^+$ (PCa+ subjects from a first institution) with $C_1^-$ (PCa− subjects from the first institution) subpopulations indicates statistically significant differences on both anterior and posterior sides of the prostate near the apex in elements 711-713. In this example, CG morphological differences are highlighted near the inferior side and are also present at the superior side near the base in elements 715-717. The PCa+ and PCa− comparison within $C_2$ (second institution) and $C_3$ (third institution) subpopulations acquired from a second institution and a third institution shows a consistent trend. Statistically significant differences are indicated near the apex on the prostate in elements 721-723 and 731-733. CG differences may be based on the volume differences between the PCa+ and PCa− subjects, due to the hypertrophy of CG.

Subpopulations may be compared by volume. In one embodiment, prostate capsule volume or CG volume may be computed after members of the set of MR images are mapped in a common frame of reference provided by the atlas. Atlas construction corrects volume differences in the prostate found in the subpopulations acquired from different institutions. Atlas alignment may indicate CG hypertrophy of a Bx− population relative to a PCa+ subpopulation, with a p-value<0.05. CG hypertrophy of the Bx− population relative to a PCa+ subpopulation may be demonstrated when comparing PCa+ and PCa− populations acquired across different institutions. A comparison of Bx+ with normal subjects may reveal consistent volumes in both prostate and CG, indicating that the normal population is similar in prostate and CG volume relative to the PCa+ subjects. In this implementation, the mean prostate and CG volumes are relatively smaller than original volumes, since aligning the atlas tends to shrink the subjects when aligning them into a common frame of reference. Example methods and apparatus improve on conventional approaches by considering volume information when quantifying differences between populations, between a patient and a statistical shape atlas, or when generating a BcR probability score. PSA-based patient screening causes an over-representation of large prostate volumes, which produce more PSA than smaller prostates. Thus, patients demonstrating elevated PSA levels but who are found to be Bx−, may suffer hypertrophy of the CG. Example methods and apparatus thus reduce PSA-related over-diagnosis compared to conventional approaches.

Figure 3:
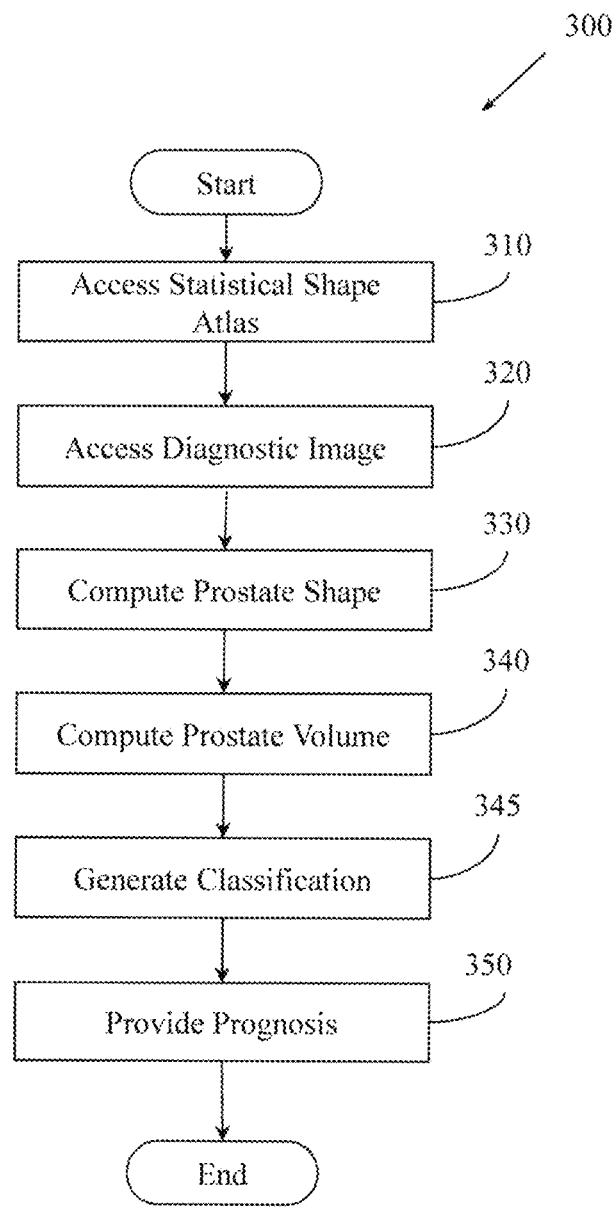
FIG. 3 illustrates an example method of producing a quantification of differences between a diagnostic image of a region of prostate tissue and a statistical shape atlas.

FIG. 3 illustrates a method 300 for producing a quantification of differences between a diagnostic image of a region of prostate tissue and a statistical shape atlas. Method 300 includes, at 310 accessing a statistical shape atlas. The statistical shape atlas includes a set of registered medical images of prostate tissue acquired from a population of subjects. In one embodiment, the population includes a subpopulation of PCa+ subjects, a subpopulation of PCa− subjects, and a subpopulation of normal subjects. A prostate represented in an image in the set of medical images includes a shape and a volume. The shape and the volume may be associated with the prostate capsule, or with the CG. The CG may include the CZ and the TZ.

Method 300 also includes, at 320, accessing a diagnostic image of a region of tissue demonstrating cancerous pathology. The diagnostic image of the region of tissue demonstrating cancerous pathology may be an MR image of a region of tissue in a patient demonstrating PCa pathology.

Method 300 also includes, at 330, computing a shape of the prostate represented in the diagnostic image. Method 300 also includes, at 340, computing a volume of the prostate represented in the diagnostic image. The shape and the volume of the prostate may be computed based, at least in part, on an annotation of an outline of the prostate capsule or the CG represented in the diagnostic image. The prostate capsule or the CG may be annotated automatically, or may be annotated by an expert pathologist.

Method 300 also includes, at 345, producing a quantification of differences between the diagnostic image of a region of prostate tissue and the statistical shape atlas. The quantification of differences may be based, at least in part, on the shape of the prostate represented in the diagnostic image, the volume of the prostate represented in the diagnostic image, and the statistical shape atlas. The quantification of differences may include a numerical or graphical representation of a difference between the diagnostic image of the region of prostate tissue and the statistical shape atlas.

Method 300 also includes, at 347, generating a classification for the region of tissue demonstrating cancerous pathology. The classification may classify the region of tissue demonstrating cancerous pathology as PCa+, PCa−, or normal. The classification may be based, at least in part, on the quantification of differences.

Method 300 also includes, at 350, providing a prognosis prediction based on the classification or the quantification of differences. Providing the prognosis prediction may include controlling a CADx system to generate a BcR probability score. The BcR probability score may be based on the classification or the quantification of differences. The BcR probability score may include a probability that a patient associated with the diagnostic image will experience BcR within a period of time. The period of time may be six months, one year, five years, or another period of time. Providing the prognosis prediction may also include displaying a numerical or graphical representation of the quantification of differences.

In one example, a method may be implemented as computer executable instructions. Thus, in one example, a computer-readable storage medium may store computer executable instructions that if executed by a machine (e.g., computer) cause the machine to perform methods described or claimed herein including method 100, method 200, and method 300. While executable instructions associated with the listed methods are described as being stored on a computer-readable storage medium, it is to be appreciated that executable instructions associated with other example methods described or claimed herein may also be stored on a computer-readable storage medium. In different embodiments, the example methods described herein may be triggered in different ways. In one embodiment, a method may be triggered manually by a user. In another example, a method may be triggered automatically.

Figure 4:
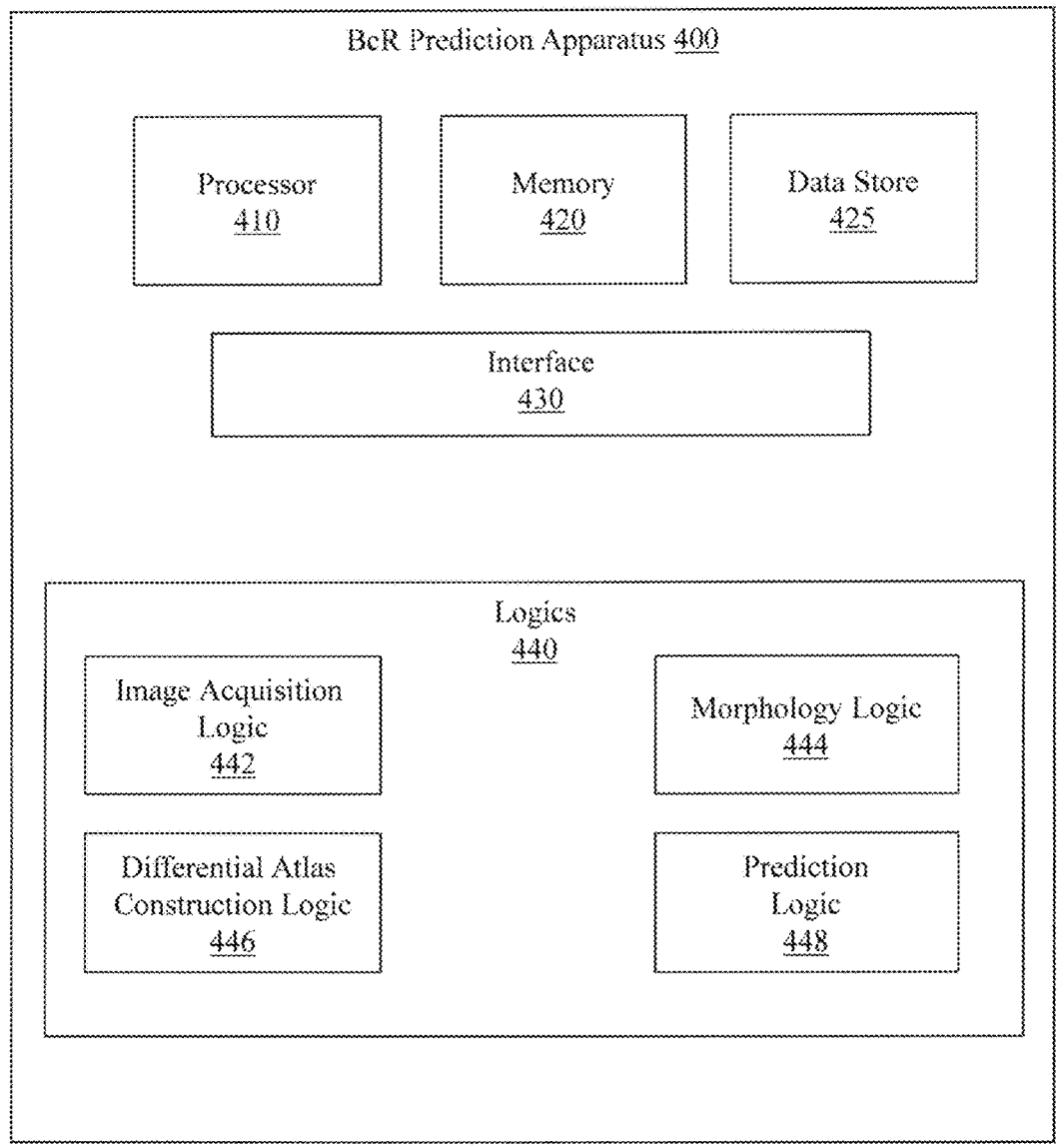
FIG. 4 illustrates an example apparatus that predicts BcR in a region of tissue demonstrating PCa pathology.

FIG. 4 illustrates an example apparatus 400 for predicting BcR in a region of tissue demonstrating PCa pathology in an image. Apparatus 400 includes a processor 410, a memory 420, a data store 425, a set of logics 440, and an interface 430 that connects the processor 410, the memory 420, the data store 425, and the set of logics 440. Data store 425 stores a set of MR images acquired from a population of subjects using a surface coil approach or an endorectal coil approach. The set of logics 440 includes an image acquisition logic 442, a morphology logic 444, a differential atlas construction logic 446, and a prediction logic 448. In one embodiment, the functionality associated with the set of logics 440 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 440 are implemented as ASICs or SOCs.

Image acquisition logic 442 acquires a diagnostic image of a region of tissue in a patient demonstrating PCa pathology. In one embodiment, image acquisition logic 442 acquires a T2w MR image of a patient demonstrating PCa pathology using a surface coil approach or an endorectal coil approach. Other imaging approaches may be used to generate and access the image accessed by image acquisition logic 442. Other image dimensions or image acquisition parameters may also be used.

Morphology logic 444 extracts a shape feature, a volume feature, or an intensity feature from the diagnostic image or from a member of the set of MR images. Morphology logic 444 generates an outline of the prostate or an outline of the CG of a member of the set of MR images or the diagnostic image by automatically detecting and annotating the prostate or the CG represented in a member of the set of MR images or the diagnostic image. The CG includes a TZ and a CZ.

Differential atlas construction logic 446 constructs a statistical shape differential atlas from the set of MR images stored in the data store 425. In one embodiment, differential atlas construction logic 446 constructs the statistical shape differential atlas by stratifying the set of MR images into a subset of MR images associated with a subpopulation of subjects. Differential atlas construction logic 446 may also stratify the set of MR images into a subset associated with an institution that acquired a member of the subset of MR images. A subject belongs to a PCa+ subpopulation, a PCa− subpopulation, or a normal population. A member of the set of MR images includes a shape feature or a volume feature. The shape feature may be associated with a prostate capsule or a CG represented in the member of the set of MR images. The volume feature may be associated with the prostate capsule or the CG represented in the member of the set of MR images. A first member of the set of MR images may be acquired using a first set of acquisition parameters, and a second member of the set of MR images may be acquired using a second, different set of acquisition parameters.

Differential atlas construction logic 446 also registers a member of the set of MR images using template-based anatomically constrained registration. The template-based anatomically constrained registration may be based on the outline of the prostate capsule represented in the member of the set of MR images, the outline of the CG in the member of the set of MR images, or a T2w MR intensity of the member of the set of MR images. In another embodiment, other registration techniques may be employed by differential atlas construction logic 446.

Differential atlas construction logic 446 also computes a spatial median for the set of MR images based, at least in part, on the shape feature or the volume feature. Differential atlas construction logic 446 may compute the spatial median based on the prostate shape feature, the CG shape feature, the prostate volume feature, or the CG volume feature. In one embodiment, differential atlas construction logic 446 also computes a median for the set of MR images based, at least in part, on the T2w MR intensity of a member of the set of MR images. The spatial median or the T2w MR intensity median may be based on a subset of the set of MR images associated with a subpopulation. Differential atlas construction logic 446 also iteratively updates the template based, at least in part, on the spatial median.

Differential atlas construction logic 446 also characterizes a statistical difference between a shape feature associated with a first subpopulation and shape feature associated with a second subpopulation. Differential atlas construction logic 446 may also characterize a statistical difference between a volume feature associated with the first subpopulation and a volume feature associated with the second subpopulation. Differential atlas construction logic 446 may employ a non-parametric per-voxel Wilcoxon test to characterize the statistical significance of morphological shape differences.

Quantification logic 448 computes a quantification of differences associated with the shape feature, the volume feature, or the intensity feature, and the differential atlas. In one embodiment, quantification logic 448 also generates a probability score for the patient based, at least in part, the quantification of differences. The quantification of differences may be based, at least in part, on the shape feature, the volume feature, or the intensity feature, and the differential atlas. In one embodiment, quantification logic 448 generates a registered diagnostic image by registering the diagnostic image to the statistical shape differential atlas. Quantification logic 448 may then control a CADx system or other medical imaging system to display the registered diagnostic image, the quantification of differences, or the BcR probability score. In one embodiment, quantification logic 448 may control a CADx system to classify the diagnostic image based, at least in part, on the quantification of differences or on the BcR probability score. In other embodiments, other types of CADx systems may be controlled, including CADx systems for types of cancer where disease classification and prognosis prediction may be based on shape or volume features quantified from MR images of a region of tissue.

In one embodiment of apparatus 400, the set of logics 440 also includes a display logic. The display logic may control the CADx system to display the quantification of differences, the BcR prediction score, the diagnostic image, members of the statistical shape differential atlas, the volume features, the registered diagnostic image, or the shape features, on a computer monitor, a smartphone display, a tablet display, or other displays. Displaying the quantification of differences, the BcR probability score, the diagnostic image, members of the atlas, or the features may also include printing the quantification of differences, the BcR probability score, the diagnostic image, members of the atlas, or the features. The display logic may also control the CADx to display an image of the region of tissue demonstrating PCa. The image of the region of tissue demonstrating PCa may include annotated representations of the prostate capsule or the CG. By displaying the diagnostic image along with the quantification of differences, the BcR probability score, or elements of the atlas, example apparatus provide a timely and intuitive way for a human pathologist to more accurately classify pathologies demonstrated by a patient, thus improving on conventional approaches to predicting cancer recurrence and disease progression.

Figure 5:
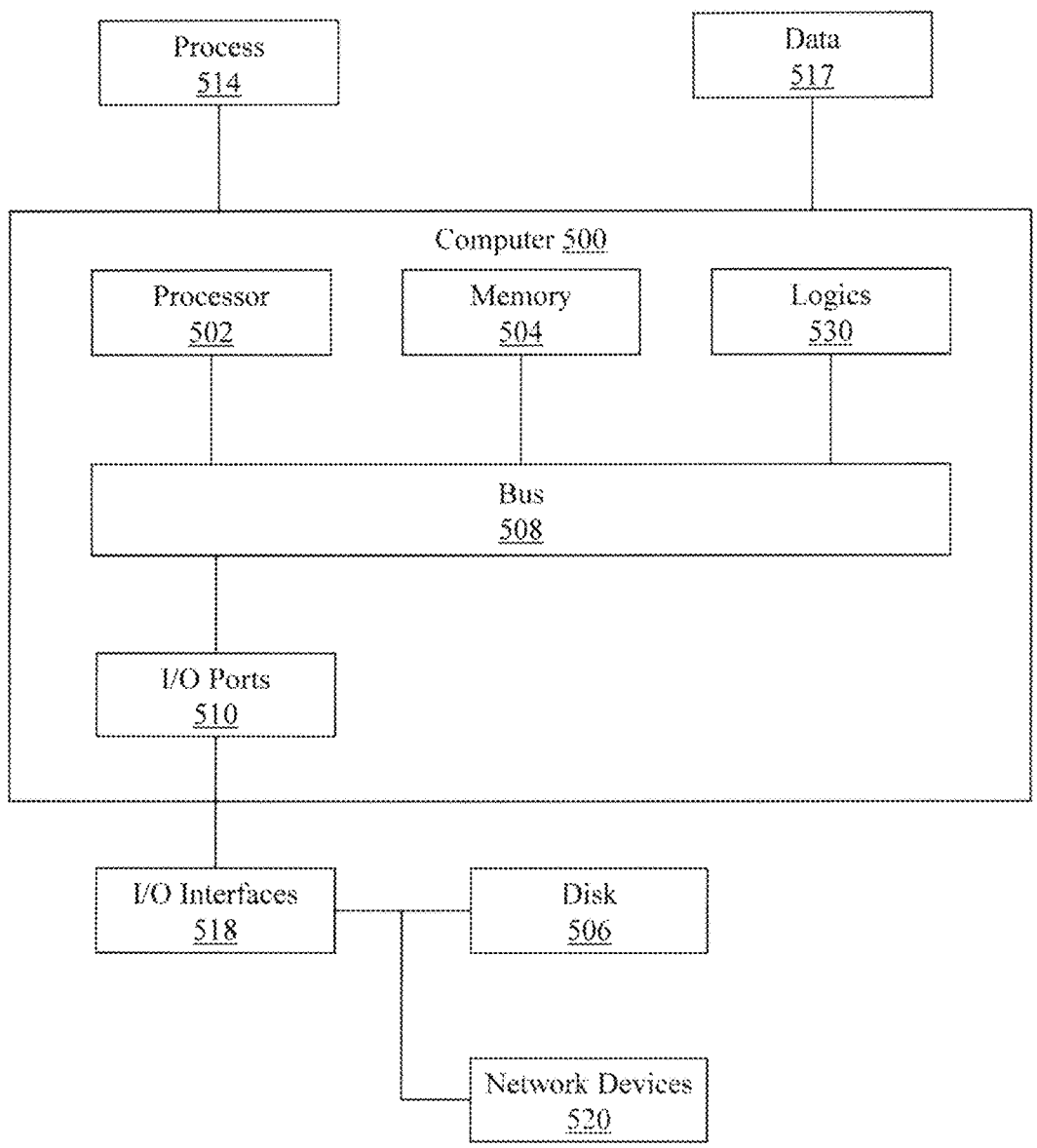
FIG. 5 illustrates an example computer in which example methods and apparatus described herein operate.

FIG. 5 illustrates an example computer 500 in which example methods illustrated herein can operate and in which example logics may be implemented. In different examples, computer 500 may be part of an MRI system, may be operably connectable to an MRI system, or may be part of a CADx system.

Computer 500 includes a processor 502, a memory 504, and input/output ports 510 operably connected by a bus 508. In one example, computer 500 may include a set of logics 530 that perform a method of predicting BcR in a region of tissue demonstrating PCa pathology. Thus, the set of logics 530, whether implemented in computer 500 as hardware, firmware, and/or a combination thereof may provide means (e.g., circuits hardware) for predicting BcR in a region of tissue demonstrating PCa pathology. In different examples, the set of logics 530 may be permanently and/or removably attached to computer 500. In one embodiment, the functionality associated with the set of logics 530 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 530 are implemented as ASICs or SOCs.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a medium that stores instructions or data. "Computer-readable storage medium" does not refer to propagated signals. A computer-readable storage medium may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage medium may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Logic", as used herein, includes but is not limited to hardware, or firmware, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage medium storing computer executable instructions that when executed by a computer control the computer to perform a method for predicting biochemical recurrence (BcR) in a region of tissue demonstrating prostate cancer (PCa) pathology, the method comprising:
   accessing a set of magnetic resonance (MR) images acquired from a population of patients, where the population includes a set of subpopulations, where a member of the set of MR images includes a prostate capsule shape attribute, a prostate capsule volume attribute, a central gland (CG) shape attribute, or a CG volume attribute;
   constructing a statistical shape atlas from the set of MR images;
   accessing an MR image of a region of prostate tissue in a patient demonstrating cancerous pathology, where the MR image of the region of prostate tissue has a prostate capsule shape attribute, a prostate capsule volume attribute, a CG shape attribute, or a CG volume attribute;
   producing a quantification of differences between the MR image of the region of prostate and the statistical shape atlas based, at least in part, on a comparison of the prostate capsule shape attribute of the MR image of the region of prostate tissue demonstrating cancerous pathology, the prostate capsule volume attribute of the MR image of the region of prostate tissue demonstrating cancerous pathology, the CG shape attribute of the MR image of the region of prostate tissue demonstrating cancerous pathology, or the CG volume attribute of the MR image of the region of prostate tissue demonstrating cancerous pathology, with the statistical shape atlas;
   computing a BcR probability score based, at least in part, on the quantification of differences, and
   controlling a computer aided diagnosis (CADx) system to generate a classification of the region of tissue in the image based, at least in part, on the BcR probability score or the quantification of differences.

2. The non-transitory computer-readable storage medium of claim 1, where the set of subpopulations includes a PCa positive (PCa+) subpopulation, a Pea negative (PCa−) subpopulation, or a normal subpopulation.

3. The non-transitory computer-readable storage medium of claim 2, where the PCa− subpopulation demonstrates increased prostate specific antigen (PSA).

4. The non-transitory computer-readable storage medium of claim 1, where the subpopulations are acquired across a plurality of institutions.

5. The non-transitory computer-readable storage medium of claim 1, the method comprising automatically annotating the prostate capsule or the CG in a member of the set of MR images or in the MR image of the region of prostate tissue demonstrating cancerous pathology.

6. The non-transitory computer-readable storage medium of claim 1, where the CG includes a prostate central zone and a prostate transitional zone.

7. The non-transitory computer-readable storage medium of claim 1, where a member of the set of MR images or the MR image of the region of prostate tissue demonstrating cancerous pathology is a 1.5 Tesla (T) T2 weighted (T2w) MR image or a 3T T2w MR image.

8. The non-transitory computer-readable storage medium of claim 1, where a first member of the set of MR images is acquired using a first set of MR acquisition parameters having a first set of values, and a second member of the set of MR images is acquired using a second, different set of MR acquisition parameters having a second, different set of values.

9. The non-transitory computer-readable storage medium of claim 8, where the first set of MR acquisition parameters and the second set of MR acquisition parameters includes pixel dimensions, resolution, or slice spacing.

10. The non-transitory computer-readable storage medium of claim 1, where the member of the set of MR images or the MR image is acquired using a surface coil or using an endorectal coil.

11. The non-transitory computer-readable storage medium of claim 2, where constructing the statistical shape atlas comprises:
   annotating a prostate capsule represented in a member of the set of MR images;
   annotating a central gland (CG) represented in the member of the set of MR images;
   upon determining that the member of the set of MR images was acquired using an endorectal coil, bias field correcting the member of the set of MR images that was acquired using an endorectal coil;
   applying template-based anatomically constrained registration to a subset of the set of MR images associated with a subpopulation, where the registration is based, at least in part, on a prostate capsule shape attribute, a prostate capsule volume attribute, a CG shape attribute, a CG volume attribute, or on a T2w intensity associated with the member of the set of MR images;
   computing a spatial median of the prostate capsule shape attribute or the CG shape attribute for the subset of the set of MR images associated with a subpopulation, or a spatial median of the prostate capsule volume attribute or the CG volume attribute for the subset;
   progressively updating a template based, at least in part, on the spatial median of the prostate capsule shape attribute, the spatial median of the CG shape attribute, the spatial median of the prostate capsule volume attribute, or the spatial median of the CG volume attribute;
   progressively increasing the complexity of an optimized three dimensional (3D) transformation, where the 3D transformation is a translation;
   correcting an atlas shift between an atlas associated with a first subpopulation and an atlas associated with a second subpopulation; and
   applying a per-voxel comparison between members of a subset of the set of MR images associated with the first subpopulation and members of a subset of a set of MR images associated with the second, different subpopulation.

12. The non-transitory computer-readable storage medium of claim 11, where progressively increasing the complexity of the optimized three dimensional (3D) transformation includes:
   converting the optimized 3D transformation from a translation to an affine translation, or converting the optimized 3D transformation from an affine translation to an elastic deformation.

13. The non-transitory computer-readable storage medium of claim 12, where correcting an atlas shift between the atlas associated with the first subpopulation and the atlas associated with the second subpopulation includes optimizing the affine translation relative to the first subpopulation and the second subpopulation, where the affine translation optimization is based, at least in part, on the prostate capsule shape attribute or the CG shape attribute.

14. The non-transitory computer-readable storage medium of claim 13 where the per-voxel comparison includes a non-parametric Wilcoxon test.

15. The non-transitory computer-readable storage medium of claim 14, where the per-voxel comparison further includes applying multiple comparison correction using a Bonferonni correction.

16. A method for producing a quantification of differences between a diagnostic image of a region of prostate tissue and a statistical shape atlas, the method comprising:
   accessing a statistical shape atlas, where the statistical shape atlas includes a set of registered medical images of prostate tissue acquired from a population of subjects, the population including a subpopulation of prostate cancer positive (PCa+) subjects, a subpopulation of, prostate cancer negative (PCa−) subjects, and a subpopulation of normal subjects, where a prostate represented in an image in the set of medical images includes a shape and a volume;
   accessing a diagnostic image of a region of tissue demonstrating cancerous pathology;
   computing a shape of the prostate represented in the diagnostic image;
   computing a volume of the prostate represented in the diagnostic image;
   producing a quantification of differences between the region of tissue demonstrating cancerous pathology and the statistical shape atlas by comparing the shape of the prostate represented in the diagnostic image, the volume of the prostate represented in the diagnostic image, and the statistical shape atlas;
   generating a classification for the region of tissue demonstrating cancerous pathology based, at least in part, on the quantification of differences; and
   providing a prognosis prediction based on the classification or the quantification of differences.

17. An apparatus for predicting biochemical recurrence (BcR) in a region of tissue demonstrating prostate cancer (PCa) pathology in an image, comprising:
   a processor;
   a memory;
   a data store that stores a set of magnetic resonance (MR) images acquired from a population of subjects using a surface coil approach or an endorectal coil approach;
   an input/output interface;
   a set of logics; and
   an interface to connect the processor, the memory, the data store, the input/output interface and the set of logics, where the set of logics includes:
      an image acquisition logic that acquires a diagnostic image of a region of tissue in a patient demonstrating PCa pathology;
      a morphology logic that extracts a shape feature, a volume feature, or an intensity feature from the diagnostic image or from a member of the set of MR images;
      a differential atlas construction logic that constructs a statistical shape differential atlas from the set of MR images; and
      a quantification logic that computes a quantification of differences associated with the shape feature, the volume feature, or the intensity feature, and the differential atlas, and that generates a BcR probability score for the patient based, at least in part, the quantification of differences.

18. The apparatus of claim 17, where the image acquisition logic acquires a T2w MR image of a patient demonstrating PCa pathology using a surface coil approach or an endorectal coil approach.

19. The apparatus of claim 17, where the morphology logic generates an outline of the prostate or an outline of the central gland (CG) of a member of the set of MR images or the diagnostic image by automatically detecting and annotating the prostate or the central gland (CG) represented in a member of the set of MR images or the diagnostic image, where the CG includes a prostate transitional zone and a prostate central zone.

20. The apparatus of claim 19, where the differential atlas construction logic:
stratifies the set of MR images into a subset of MR images associated with a subpopulation of subjects, where a subject belongs to a PCa+ subpopulation, a PCa− subpopulation, or a normal population, where a member of the set of MR images includes a shape feature or a volume feature, where the shape feature is associated with a prostate capsule or a CG represented in the member of the set of MR images, where the volume feature is associated with the prostate capsule or the CG represented in the member of the set of MR images, and where a first member of the set of MR images is acquired using a first set of acquisition parameters, and a second member of the set of MR images is acquired using a second, different set of acquisition parameters;
registers a member of the set of MR images using template-based anatomically constrained registration based on the outline of the prostate capsule represented in the member of the set of MR images, the outline of the CG in the member of the set of MR images, or a T2w MR intensity of the member of the set of MR images;
computes a spatial median for the set of MR images based, at least in part, on the shape feature or the volume feature;
iteratively updates a template based, at least in part, on the spatial median; and
characterizes a statistical difference between a shape feature associated with a first subpopulation and shape feature associated with a second subpopulation, or between a volume feature associated with the first subpopulation and a volume feature associated with the second subpopulation.

21. The apparatus of claim 17, where the quantification logic generates a registered diagnostic image by registering the diagnostic image to the statistical shape differential atlas, and controls a computer assisted diagnostic (CADx) system to display the registered diagnostic image, the quantification of differences, or the BcR probability score.

* * * * *